(12) United States Patent
Kell et al.

(10) Patent No.: US 10,217,208 B2
(45) Date of Patent: *Feb. 26, 2019

(54) APPARATUS AND A METHOD OF INSPECTING A TURBOMACHINE

(71) Applicant: ROLLS-ROYCE PLC, London (GB)

(72) Inventors: James Kell, Nottingham (GB); Adriano Pulisciano, Birmingham (GB); Thomas Frederick Danvers, Wirksworth (GB); Graeme Eric Rigg, Derby (GB)

(73) Assignee: ROLLS-ROYCE PLC, London (GB)

( * ) Notice: Subject to any disclaimer, the term of this patent is extended or adjusted under 35 U.S.C. 154(b) by 335 days.

This patent is subject to a terminal disclaimer.

(21) Appl. No.: 15/219,973

(22) Filed: Jul. 26, 2016

(65) Prior Publication Data

US 2016/0335761 A1 Nov. 17, 2016

Related U.S. Application Data

(60) Continuation of application No. 14/940,964, filed on Nov. 13, 2015, now abandoned, which is a division of
(Continued)

(30) Foreign Application Priority Data

Nov. 28, 2011 (GB) .................................. 1120419.5

(51) Int. Cl.
*H04N 7/18* (2006.01)
*G06T 7/00* (2017.01)
(Continued)

(52) U.S. Cl.
CPC .............. *G06T 7/0008* (2013.01); *F01D 5/12* (2013.01); *F01D 9/041* (2013.01); *F01D 21/003* (2013.01);
(Continued)

(58) Field of Classification Search
CPC .......... H04N 7/183; H04N 7/18; H04N 7/185; F01D 25/285
(Continued)

(56) References Cited

U.S. PATENT DOCUMENTS 4,702,229 A 10/1987 Zobel
4,721,098 A 1/1988 Watanabe
(Continued)

FOREIGN PATENT DOCUMENTS

EP 1 975 271 A2 10/2008
EP 2 119 875 A2 11/2009
(Continued)

OTHER PUBLICATIONS

Mar. 13, 2012 British Search Report issued in Application No. 1120419.5.
(Continued)

*Primary Examiner* — Sherrie Hsia
(74) *Attorney, Agent, or Firm* — Oliff PLC (57) ABSTRACT

An apparatus for inspecting a turbomachine includes a plurality of boroscopes, a device to rotate the rotor of the turbomachine and a processor having reference measurements of the rotor blades and/or reference measurements between the rotor blades and the boroscopes. A boroscope is inserted in a casing aperture upstream of the blades to view the leading edge and a portion of one of the surfaces of each blade as the rotor is rotated. A boroscope is inserted in a casing aperture downstream of the blades to view the trailing edge and a portion of one of the surfaces of each blade as the rotor is rotated. The boroscopes supply the images of each of the blades to the processor. The processor analyses the images of the blades and uses the reference measurements to determine the position and size of any defect on any of the rotor blades.

20 Claims, 3 Drawing Sheets

Related U.S. Application Data application No. 13/675,689, filed on Nov. 13, 2012, now Pat. No. 9,300,926.

(51) Int. Cl.

| | |
|---|---|
| *F01D 25/28* | (2006.01) |
| *F01D 5/12* | (2006.01) |
| *F01D 9/04* | (2006.01) |
| *G01M 15/14* | (2006.01) |
| *G02B 23/24* | (2006.01) |
| *F01D 25/24* | (2006.01) |
| *G01N 21/954* | (2006.01) |
| *H04N 5/247* | (2006.01) |
| *F01D 21/00* | (2006.01) |
| *H04N 5/225* | (2006.01) |

(52) U.S. Cl.
CPC ........... *F01D 25/24* (2013.01); *F01D 25/285* (2013.01); *G01M 15/14* (2013.01); *G01N 21/954* (2013.01); *G02B 23/24* (2013.01); *H04N 5/247* (2013.01); *H04N 7/183* (2013.01); *F05D 2220/32* (2013.01); *F05D 2260/80* (2013.01); *F05D 2260/83* (2013.01); *G01N 2021/9542* (2013.01); *G06T 2207/30164* (2013.01); *H04N 2005/2255* (2013.01)

(58) Field of Classification Search
USPC .......................... 348/82, 85, 83, 92; 600/109
See application file for complete search history.

(56) References Cited

U.S. PATENT DOCUMENTS

| | | |
|---|---|---|
| 4,820,043 A | 4/1989 | Diener |
| 4,825,259 A | 4/1989 | Berry, Jr. |
| 4,895,431 A | 1/1990 | Tsujiuchi et al. |
| 4,935,810 A | 6/1990 | Nonami et al. |
| 5,432,543 A | 7/1995 | Hasegawa et al. |
| 5,547,455 A | 8/1996 | McKenna et al. |
| 5,800,341 A | 9/1998 | McKenna et al. |
| 6,009,189 A | 12/1999 | Schaack |
| 6,450,950 B2 | 9/2002 | Irion |
| 2005/0199832 A1 | 9/2005 | Twerdochlib |
| 2007/0258807 A1 | 11/2007 | Brummel |
| 2011/0090514 A1* | 4/2011 | Robinson ............... F01D 5/005 356/601 |

FOREIGN PATENT DOCUMENTS

| | | |
|---|---|---|
| GB | 1 296 534 A | 11/1972 |
| GB | 2 033 973 A | 5/1980 |
| JP | 2005077832 A | 3/2005 |

OTHER PUBLICATIONS

Feb. 26, 2016 Office Action issued in U.S. Appl. No. 14/940,964.
Jan. 12, 2018 European Search Report issued in European Application No. 12 19 2160.

* cited by examiner

APPARATUS AND A METHOD OF INSPECTING A TURBOMACHINE

This is a continuation of application Ser. No. 14/940,964, filed on Nov. 13, 2015, now abandoned, which is a division of application Ser. No. 13/675,689, filed on Nov. 13, 2012, now U.S. Pat. No. 9,300,926, which claims priority to United Kingdom Patent Application No. 1120419.5, filed Nov. 28, 2011. The disclosure of the prior applications is hereby incorporated by reference herein in its entirety.

The present invention relates to an apparatus and a method of inspecting a turbomachine and in particular to an apparatus and a method of inspecting a gas turbine engine.

Currently in-situ inspection of a gas turbine engine takes place using a manually controlled flexible videoscope. In the inspection process the flexible videoscope is inserted through an inspection aperture in a casing of the gas turbine engine and manipulated such that the flexible videoscope is able to view the rotor blades of a stage of rotor blades of the gas turbine engine. Images are taken of interesting features, i.e damage, on the rotor blades or of random rotor blades to illustrate the level of contamination or generic degradation of the rotor blades. The tip of the videoscope is attached to a flexible insertion tube that may be articulated remotely by an operator who feeds the insertion tube through the inspection aperture in the casing of the gas turbine engine. The flexible videoscope is then inserted through another inspection aperture in the casing of the gas turbine engine and manipulated such that the flexible videoscope is able to view the rotor blades of another stage of rotor blades of the gas turbine engine. The images are analysed to determine whether to repair damage to the engine, remove the engine or allow continued operation of the engine.

Currently the time to carry out an in-situ inspection of a gas turbine engine is about 8 to 10 hours. The inspection process requires highly skilled operators to perform the inspection process. During the analysis of the images the operators often have difficulty determining which component the images relate to.

UK patent GB1296534 discloses a method of inspecting the stator vanes of a gas turbine engine using a boroscope. The distal end of the boroscope is provided with an inflatable bag. The boroscope is inserted into the gas turbine engine through an aperture in a casing and after the boroscope has been inserted into the gas turbine engine the bag is inflated between two adjacent rotor blades located on a rotor of the gas turbine engine such that the bag grips and locates the distal end of the boroscope between the rotor blades. The rotor is then rotated to move the boroscope from stator vane to stator vane so that the boroscope is able to view the edges of the stator vanes of the gas turbine engine.

UK patent application GB2033973A discloses a method of inspecting the stator vanes and/or rotor blades of a gas turbine engine using a boroscope. A shaped guide tube is inserted into the gas turbine engine through an aperture in a casing and a distal end of the guide tube is positioned adjacent a stator vane or a rotor blade to be viewed. A boroscope is guided by the guide tube to the stator vane or rotor blade. The guide tube is moved radially so that the boroscope is able to view the full radial span of the stator vane or rotor blade. All of the rotor blades are inspected by rotating the rotor so that each rotor blade passes in front of the boroscope. All of the stator vanes are inspected by positioning the guide tube in other suitable apertures in the casing.

European patent application EP2119875A2 discloses a method of inspecting stationary components, stator vanes, of a gas turbine engine using an inspection element. The inspection element is positioned on a rotor of the gas turbine engine. The rotor is rotated so that the inspection element is able to view the stationary components. Data is transmitted via a wireless link from the inspection element. The inspection element may be a boroscope or a camera.

Accordingly the present invention seeks to provide an apparatus and method of inspecting a turbomachine which reduces, preferably overcomes, the above mentioned problems.

Accordingly the present invention provides a method of inspecting a turbomachine, the turbomachine comprising a rotor having at least one stage of rotor blades and a casing surrounding the rotor and at least one stage of rotor blades, each rotor blade comprising a platform portion and an aerofoil portion, the aerofoil portion having a leading edge, a trailing edge, a concave surface, a convex surface and a tip, the method comprising the steps of a) providing a plurality of boroscopes, b) inserting each boroscope through a respective one of a plurality of apertures in a casing of the turbomachine, at least one of the apertures in the casing being upstream of the rotor blades, at least one of the apertures in the casing being downstream of the rotor blades, c) rotating the rotor of the turbomachine, d) providing reference measurements of the rotor blades and/or reference measurements between the rotor blades and the boroscopes, e) viewing the leading edge and at least a portion of the concave surface or viewing the leading edge and at least a portion of the convex surface of each of the rotor blades of the turbomachine as the rotor is rotated using the boroscope in the at least one of the apertures in the casing upstream of the rotor blades and supplying the image of each of the rotor blades to the processor, f) viewing the trailing edge and at least a portion of the convex surface or viewing the trailing edge and at least a portion of the concave surface of each of the rotor blades of the turbomachine as the rotor is rotated using the boroscope in the at least one of the apertures in the casing downstream of the rotor blades and supplying the image of each of the rotor blades to the processor, and g) analysing the images of the rotor blades and using the reference measurements of the rotor blades and/or reference measurements between the rotor blades and the boroscopes to determine the position and size of any defect on any of the rotor blades.

The reference measurements of the rotor blades may be the measurement from the platform portion to the tip of the aerofoil portion of the rotor blade and/or the measurement from the leading edge to the trailing edge of the aerofoil portion of the rotor blade.

The method may comprise providing a model of the rotor and the at least one stage of rotor blades.

The method may comprise placing the image of the leading edge and at least a portion of the concave surface or placing the image of the leading edge and at least a portion of the convex surface of each of the rotor blades of the turbomachine onto corresponding positions of the model of the rotor and rotor blades and placing the image of the trailing edge and at least a portion of the convex surface or placing the image of the trailing edge and at least a portion of the concave surface of each of the rotor blades of the turbomachine onto corresponding positions of the model of the rotor and rotor blades.

Each boroscope may comprise a rigid structure and at least one camera arranged at a predetermined longitudinal position, the at least one camera is arranged with a line of sight transverse to the longitudinal direction of the boroscope.

At least one of the boroscopes may comprise a plurality of cameras. A plurality of boroscopes may comprise a plurality of cameras.

At least one of the boroscopes may comprise a plurality of cameras at the predetermined longitudinal position and the cameras are arranged with lines of sight arranged at different angles. A plurality of the boroscopes may comprise a plurality of cameras at the predetermined longitudinal position and the cameras are arranged with lines of sight arranged at different angles.

At least one of the boroscopes may comprise a plurality of cameras at different longitudinal positions. A plurality of the boroscopes may comprise a plurality of cameras at different longitudinal positions.

The method may comprise supplying the image of each of the rotor blades from each of the cameras at the different longitudinal positions of the boroscope to the processor, the processor producing a composite image of each of the rotor blades from the images supplied by the plurality of cameras.

The method may comprise placing the composite image of each of the rotor blades of the turbomachine onto corresponding positions of the model of the rotor and rotor blades.

At least one of the boroscopes may comprise at least one camera arranged with a line of sight directed in a downstream direction towards a stage of rotor blades and at least one camera arranged with a line of sight directed in an upstream direction towards a stage of rotor blades. A plurality of the boroscopes may comprise at least one camera arranged with a line of sight directed in a downstream direction towards a stage of rotor blades and at least one camera arranged with a line of sight directed in an upstream direction towards a stage of rotor blades.

At least one of the boroscopes may comprise a plurality of cameras at different longitudinal positions arranged with a line of sight directed in the downstream direction towards a stage of rotor blades and a plurality of cameras at different longitudinal positions arranged with a line of sight in the upstream direction towards a stage of rotor blades.

The method may comprise providing a measurement of the angular position of the rotor relative to the boroscopes, supplying the measurement of the angular position of the rotor to the processor and relating the images of each of the rotor blades to the corresponding rotor blade on the rotor.

The turbomachine may comprise a stage of stator vanes upstream of the at least one stage of rotor blades and a stage of stator vanes downstream of the at least one stage of rotor blades, step b) comprising inserting a boroscope between two adjacent stator vanes of the stage of stator vanes upstream of the at least one stage of rotor blade and inserting a boroscope between two adjacent stator vanes of the stage of stator vanes downstream of the at least one stage of rotor blades.

Step b) may comprise placing a boroscope upstream of each one of a plurality of stages of rotor blades and placing a boroscope downstream of each one of the plurality of stages of rotor blades, step d) comprises providing reference measurements of the rotor blades of each of the stages of rotor blades and/or reference measurements between the rotor blades of each of the stages of rotor blades and the corresponding boroscopes and step g) comprises analysing the images of the rotor blades of each of the stages of rotor blades and using the reference measurements of the rotor blades for each stage of rotor blades and/or reference measurements between the rotor blades of each stage of rotor blades and the corresponding boroscopes to determine the position and size of any defect on any of the rotor blades.

Step b) may comprise placing a single boroscope upstream of a stage of rotor blades and downstream of a stage of rotor blades, step e) comprises viewing the leading edge and at least a portion of the concave surface or viewing the leading edge and at least a portion of the convex surface of each of the rotor blades of the stage of rotor blades downstream of the boroscope as the rotor is rotated using the boroscope and supplying the image of each of the rotor blades to the processor, and step f) comprises viewing the trailing edge and at least a portion of the convex surface or viewing the trailing edge and at least a portion of the concave surface of each of the rotor blades upstream of the boroscope as the rotor is rotated using the boroscope and supplying the image of each of the rotor blades to the processor.

The rotor may be a compressor rotor and the rotor blades are compressor blades.

The rotor may be a turbine rotor and the rotor blades are turbine blades.

The turbomachine may be a gas turbine engine.

The turbomachine may be a steam turbine or a water turbine.

The present invention also provides a method of inspecting a turbomachine, the turbomachine comprising a rotor having at least one stage of rotor blades and a casing surrounding the rotor and at least one stage of rotor blades, each rotor blade comprising a platform portion and an aerofoil portion, the aerofoil portion having a leading edge, a trailing edge, a concave surface, a convex surface and a tip, the method comprising the steps of a) providing a plurality of boroscopes, b) inserting each boroscope through a respective one of a plurality of apertures in a casing of the turbomachine, at least one of the apertures in the casing being upstream of the rotor blades, at least one of the apertures in the casing being downstream of the rotor blades, c) rotating the rotor of the turbomachine, d) providing a processor having a model of the rotor and the at least one stage of rotor blades, e) viewing the leading edge and at least a portion of the concave surface or viewing the leading edge and at least a portion of the convex surface of each of the rotor blades of the turbomachine as the rotor is rotated using the boroscope in the at least one of the apertures in the casing upstream of the rotor blades and supplying the image of each of the rotor blades to the processor, f) viewing the trailing edge and at least a portion of the convex surface or viewing the trailing edge and at least a portion of the concave surface of each of the rotor blades of the turbomachine as the rotor is rotated using the boroscope in the at least one of the apertures in the casing downstream of the rotor blades and supplying the image of each of the rotor blades to the processor, and g) placing the image of the leading edge and at least a portion of the concave surface or the leading edge and at least a portion of the convex surface of each of the rotor blades of the turbomachine onto corresponding positions of the model of the rotor and rotor blades and placing the image of the trailing edge and at least a portion of the convex surface or the trailing edge and at least a portion of the concave surface of each of the rotor blades of the turbomachine onto corresponding positions of the model of the rotor and rotor blades.

The present invention also provides an apparatus for inspecting a turbomachine, the turbomachine comprising a rotor having at least one stage of rotor blades and a casing surrounding the rotor and at least one stage of rotor blades, each rotor blade comprising a platform portion and an aerofoil portion, the aerofoil portion having a leading edge, a trailing edge, a concave surface, a convex surface and a tip, the casing of the turbomachine having a plurality of apertures, at least one of the apertures in the casing being upstream of the rotor blades and at least one of the apertures in the casing being downstream of the rotor blades, the apparatus comprising a plurality of boroscopes, each boroscope being insertable through a respective one of the plurality of apertures in the casing of the turbomachine, a device to rotate the rotor of the turbomachine, a processor having reference measurements of the rotor blades and/or reference measurements between the rotor blades and the boroscopes, at least one of the boroscopes inserted in at least one of the apertures in the casing upstream of the rotor blades being arranged to view the leading edge and at least a portion of the concave surface or being arranged to view the leading edge and at least a portion of the convex surface of each of the rotor blades of the turbomachine as the rotor is rotated, the at least one of the boroscopes being arranged to supply the image of the leading edge and at least a portion of the concave surface or being arranged to supply the image of the leading edge and at least a portion of the convex surface of each of the rotor blades of the turbomachine as the rotor is rotated, at least one of the boroscopes inserted in at least one of the apertures in the casing downstream of the rotor blades being arranged to view trailing edge and at least a portion of the convex surface or being arranged to view the trailing edge and at least a portion of the concave surface of each of the rotor blades of the turbomachine as the rotor is rotated, the at least one of the boroscopes being arranged to supply the image of the trailing edge and at least a portion of the convex surface or being arranged to supply the image of the trailing edge and at least a portion of the concave surface of each of the rotor blades of the turbomachine as the rotor is rotated, the processor being arranged to analyse the images of the rotor blades and to use the reference measurements of the rotor blades and/or reference measurements between the rotor blades and the boroscopes to determine the position and size of any defect on any of the rotor blades.

The present invention also provides a boroscope comprising a rigid structure and a plurality of cameras, each camera is arranged at a predetermined longitudinal position, each camera is arranged with a line of sight transverse to the longitudinal direction of the boroscope.

The boroscope may comprise a plurality of cameras at the predetermined longitudinal position and the cameras are arranged with lines of sight arranged at different angles.

The boroscope may comprise a plurality of cameras at different longitudinal positions.

The boroscope may comprise at least one camera arranged with a line of sight directed in a first direction and at least one camera arranged with a line of sight directed in a second direction opposite to the first direction.

The boroscope may comprise a plurality of cameras at different longitudinal positions arranged with a line of sight in the first direction and a plurality of cameras at different longitudinal positions arranged with a line of sight in the second direction.

The present invention will be more fully described with reference to the accompanying drawings, in which: —

Figure 1:
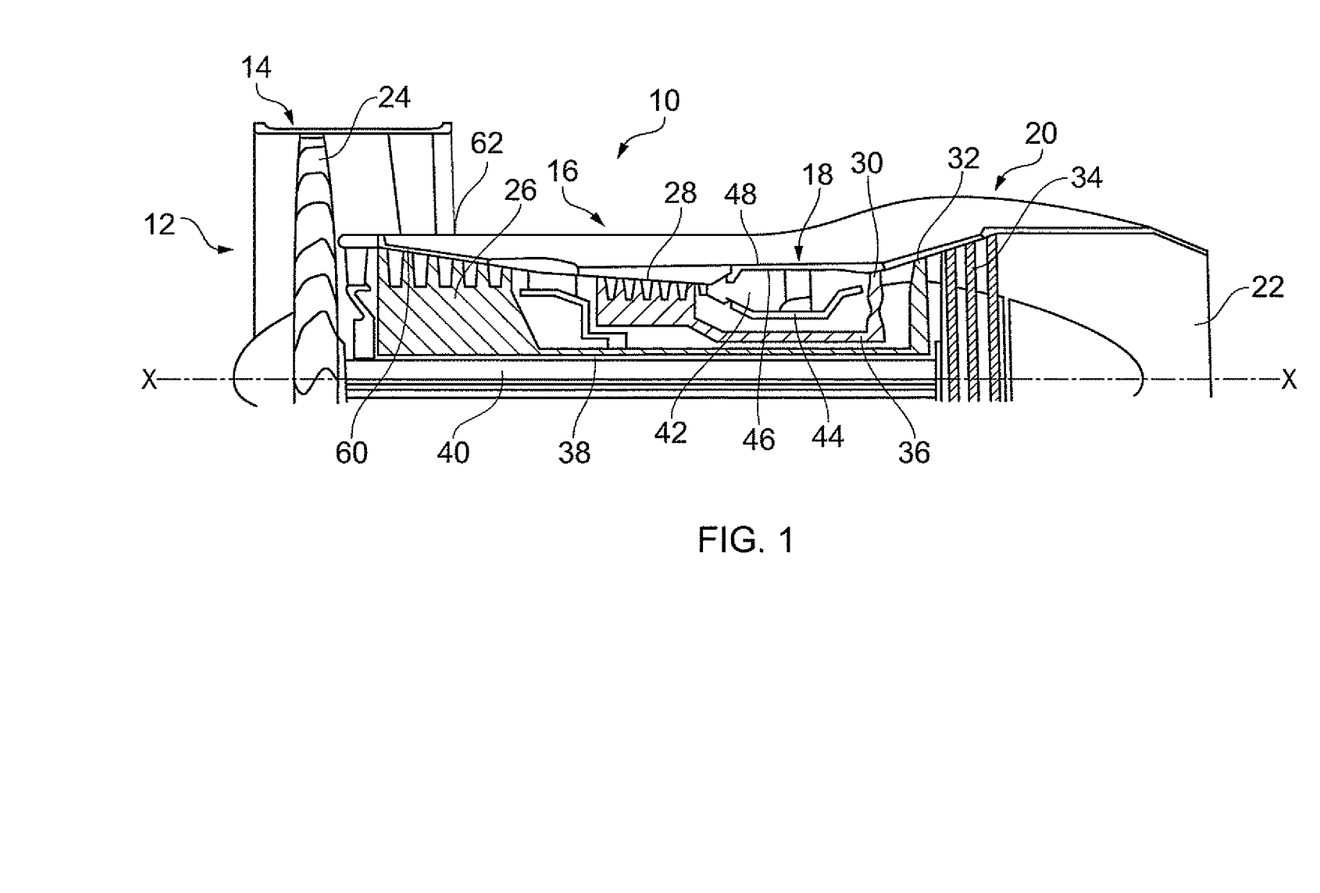
FIG. 1 is a cross-sectional view through a turbofan gas turbine engine.

A turbofan gas turbine engine 10, as shown in FIG. 1, comprises in flow series an inlet 12, a fan section 14, a compressor section 16, a combustion section 18, a turbine section 20 and an exhaust 22. The fan section 14 comprises a fan 24. The compressor section 16 comprises in flow series an intermediate pressure compressor 26 and a high pressure compressor 28. The turbine section 20 comprises in flow series a high pressure turbine 30, an intermediate pressure turbine 32 and a low pressure turbine 34. The fan 24 is driven by the low pressure turbine 34 via a shaft 40. The intermediate pressure compressor 26 is driven by the intermediate pressure turbine 32 via a shaft 38 and the high pressure compressor 28 is driven by the high pressure turbine 30 via a shaft 36. The turbofan gas turbine engine 10 operates quite conventionally and its operation will not be discussed further. The turbofan gas turbine engine 10 has a rotational axis X.

Figure 2:
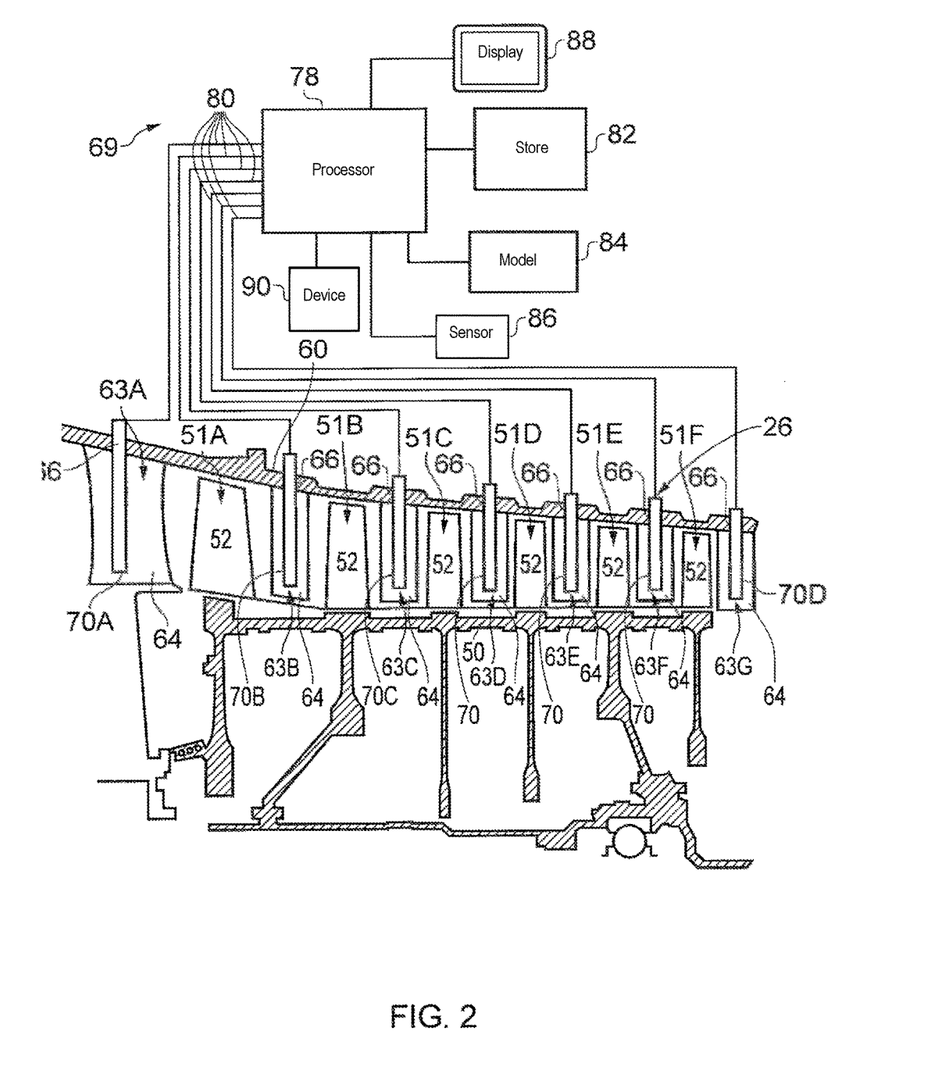
FIG. 2 is an enlarged cross-sectional view through an intermediate pressure compressor of the turbofan gas turbine engine shown in FIG. 1 and an apparatus for inspecting a gas turbine engine according to the present invention.

The intermediate pressure compressor 26, as shown in FIG. 2, comprises a rotor 50 having a plurality of axially spaced stages 51A, 51B, 51C, 51D, 51E and 51F of rotor blades 52. The rotor blades 52 in each stage 51A, 51B, 51C, 51D, 51E and 51F of rotor blades 52 are circumferentially spaced and extend radially outwardly from the rotor 50. Each rotor blade 52 comprises a root portion 51, a platform portion 53 and an aerofoil portion 54. The aerofoil portion 54 of each rotor blade 50 comprises a leading edge 55, a trailing edge 57, a concave surface 59, a convex surface 61 and a tip 63. The root portion 54 of each rotor blade 52 may have a dovetail shape or a firtree shape. The root portion 54 of each rotor blade 52 locates in a groove 58 in the rim 56 of the rotor 50. If the root portions 54 of all of the rotor blades 52 in a stage 51A, 51B, 51C, 51D, 51E and 51F of rotor blades have a dovetail shape then the root portions 54 of all the rotor blades 52 locate in a circumferentially extending, dovetail shape, groove 58 in the rim 56 of the rotor 50. If the root portions 54 of all of the rotor blades 52 in a stage 51A, 51B, 51C, 51D, 51E and 51F of rotor blades have a firtree shape then the root portion 54 of each rotor blade 52 locates in a corresponding one of a plurality of circumferentially spaced, axially extending, firtree shape, grooves 58 in the rim 56 of the rotor 50.

The intermediate pressure compressor 26 also comprises an inner casing 60 surrounding the rotor 50 and rotor blades 52 and an outer casing 62 surrounding the inner casing 60. The inner casing 60 carries a plurality of axially spaced stages 63A, 63B, 63C, 63D, 63E, 63F and 63G of stator vanes 64. The stator vanes 64 in each stage 63A, 63B, 63C, 63D, 63E, 63F and 63G of stator vanes 64 are circumferentially spaced and extend radially inwardly from the inner casing 60. The radially outer ends of the stator vanes 64 of each stage 63A, 63B, 63C, 63D, 63E, 63F and 63G of stator vanes 64 are secured to the inner casing 60. The stages 51A, 51B, 51C, 51D, 51E and 51F of rotor blades 52 and the stages 63A, 63B, 63C, 63D, 63E, 63F and 63G of stator vanes 64 are arranged axially alternately through the intermediate pressure compressor 26. The inner casing 60 and the outer casing 62 have a plurality of aligned, e.g. coaxial, inspection apertures 66 and 68 respectively. At least one pair of aligned apertures 66 and 68 is arranged axially between a respective pair of axially adjacent stages 51A and 51B or 51B and 51C of rotor blades 52 and circumferentially between an adjacent pair of stator vanes 64 in the stage 63B of stator vanes 64 between the axially adjacent stages 51A, 51B or 51B, 51C of rotor blades 62. In addition one pair of aligned apertures 66 and 68 is arranged axially upstream of the axially upstream stage, the first stage 51A, of rotor blades 52 and circumferentially between an adjacent pair of stator vanes 64 in the stage 63A of stator vanes 64 upstream of the axially upstream stage 51A of rotor blades 62. In addition one pair of aligned apertures 66 and 68 is arranged axially downstream of the axially downstream stage, the last stage, 51F of rotor blades 52 and circumferentially between an adjacent pair of stator vanes 64 in the last stage 63G of stator vanes 64 downstream of the axially downstream stage 51F of rotor blades 62.

Figure 3:
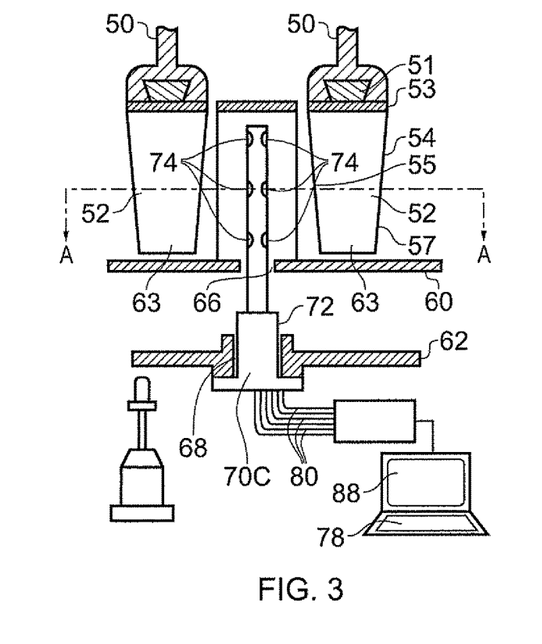
FIG. 3 is a further enlarged view of a portion of the intermediate pressure compressor and one of the boroscopes of the apparatus for inspecting a gas turbine engine according to the present invention.
Figure 4:
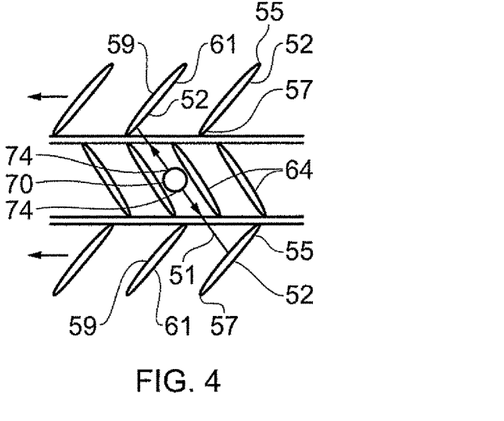
FIG. 4 is a cross-sectional view in the direction of arrows A-A in FIG. 3.
Figure 6:
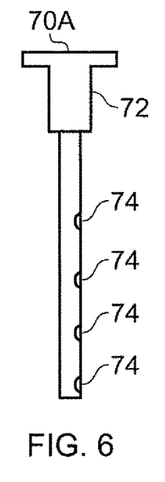
FIG. 6 is a view of a first type of boroscope of the apparatus for inspecting a gas turbine engine according to the present invention.
Figure 7:
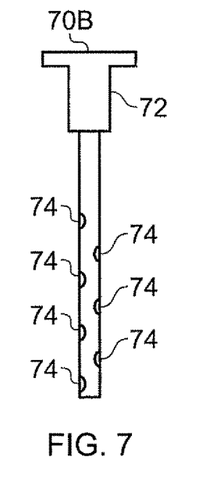
FIG. 7 is a view of a second type of boroscope of the apparatus for inspecting a gas turbine engine according to the present invention.
Figure 8:
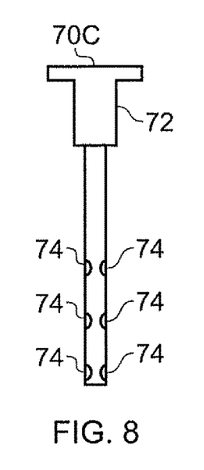
FIG. 8 is a view of an alternative third type of boroscope of the apparatus for inspecting a gas turbine engine according to the present invention.

FIGS. 2 to 4 also show an apparatus 69 for inspecting the gas turbine engine 10. The apparatus 69 comprises a plurality of boroscopes 70 and each boroscope 70 is located in a respective one of the pairs of aligned apertures 66 and 68 in the inner and outer casings 60 and 62 respectively. Each of the boroscopes 70 comprises a rigid structure 72 and at least one camera 74. Each of the boroscopes 70 is secured to the outer casing 62 while it is in the associated aperture 68 in the outer casing 62, for example each boroscope 70 is fastened to the outer casing 62 by bolts locating in threaded holes around the associated aperture 68. The at least one camera 74 is arranged at a predetermined longitudinal position and the at least one camera 74 is arranged with a line of sight transverse to the longitudinal direction of the boroscope 70. Each boroscope 70 is unique, and is different to all of the other boroscopes 70. The boroscope 70 upstream of the first stage, upstream stage, 51A of rotor blades 52 may have four or five cameras 74 at four or five predetermined longitudinal positions and each camera 74 is arranged with a line of sight directed in a downstream direction towards the first stage, upstream stage, 51A of rotor blades 52, as shown in FIG. 6. The boroscope 70 downstream of the downstream stage, last stage, 51F of rotor blades 52 has one camera 74 at a predetermined longitudinal position and the camera 74 is arranged with a line of sight directed in an upstream direction towards the downstream stage, last stage, 51F of rotor blades 52, as shown in FIG. 8. Each boroscope 70 positioned between a pair of axially adjacent stages 51A and 51B or 51B and 51C of rotor blades 52 comprises at least one camera 74 arranged with a line of sight S1 directed in a downstream direction towards a stage 51B or 51C respectively of rotor blades 52 and at least one camera 74 arranged with a line of sight S2 directed in an upstream direction towards a stage 51A or 51B respectively of rotor blades 52, as shown in FIG. 7. The number of cameras 74 on a particular boroscope 74 is determined by the radial length of the rotor blades 52 and the requirement that the camera, or cameras, produce a full image of the rotor blades 52. Each camera 74 is located at a predetermined position on the boroscope 70 such that a full image of the rotor blades 52 is obtained. Some of the boroscopes 70 may comprise a plurality of cameras 74 arranged at different longitudinal positions. Each camera 74 on each boroscope 70 also has an associated light source 76 to illuminate the rotor blades 52. The cameras 74 on boroscopes 70 with a plurality of cameras 74 are arranged such that the fields of view of the cameras 74 overlap to ensure that the images of the cameras 74 may be amalgamated together to produce a full image of the rotor blades 52.

The apparatus 69 also comprises a processor 78, for example a personal computer, and each camera 74 of each boroscope 70 is connected to the processor 78 by a respective cable 80 so as to supply images from the respective camera 74 to the processor 78. The processor 78 has a store 82 containing reference measurements of the rotor blades 52 in each stage of rotor blades 52 and/or has reference measurements between the rotor blades 52 in each stage of rotor blades 52 and the boroscope 70 upstream of the stage of rotor blades 52 and/or reference measurements between the rotor blades 52 in each stage of rotor blades 52 and the boroscope 70 downstream of the stage of rotor blades 52. The processor 78 has a model 84 of the rotor 50 and each stage of rotor blades 52. The reference measurements of the rotor blades 52 may be the measurement from the platform portion 53 to the tip 63 of the rotor blade 52 for the respective stage of rotor blades 52 and/or the measurement from the leading edge 55 to the trailing edge 57 of the rotor blade 52 for the respective stage of rotor blades 52. The apparatus 69 also comprises a sensor 86 which provides a measurement of the angular position of the rotor 50 relative to the boroscopes 70 and the measurement of the angular position of the rotor 50 is supplied to the processor 78. The apparatus 69 additionally comprises a display 88 connected to the processor 78. The apparatus 69 further comprises a device 90 arranged to rotate the rotor 50.

A method of inspecting a gas turbine engine 10 according to the present invention is described with reference to FIGS. 2 to 4. The method of inspecting the gas turbine engine 10 comprises providing a plurality of boroscopes 70, inserting each boroscope 70 through a respective one of a plurality of apertures 66, 68 in a casing 62, 64 of the gas turbine engine 10, at least one of the apertures 66, 68 in the casing 62, 64 is upstream of the rotor blades 52 and at least one of the apertures 66, 68 in the casing 62, 64 is downstream of the rotor blades 52. The rotor 50 of the gas turbine engine 10 is rotated. Reference measurements of the rotor blades 52 and/or reference measurements between the rotor blades 52 and the boroscopes 70 are provided. The leading edge 55 and at least a portion of the concave surface 59 or the leading edge 55 and at least a portion of the convex surface 61 of each of the rotor blades 52 of the gas turbine engine 10 are viewed as the rotor 50 is rotated using the boroscope 70 in the at least one of the apertures 66, 68 in the casing 62, 64 upstream of the rotor blades 52 and the image of each of the rotor blades 52 is supplied to the processor 78. The trailing edge 57 and at least a portion of the convex surface 61 or the trailing edge 57 and at least a portion of the concave surface 59 of each of the rotor blades 52 of the gas turbine engine 10 are viewed as the rotor 50 is rotated using the boroscope 70 in the at least one of the apertures 66, 68 in the casing 62, 64 downstream of the rotor blades 52 and the image of each of the rotor blades 52 is supplied to the processor 78. The processor 78 analyses the images of the rotor blades 52 and uses the reference measurements of the rotor blades 52 and/or reference measurements between the rotor blades 52 and the boroscopes 70 to determine the position and size of any defect on any of the rotor blades 52.

The processor 78 places the image of the leading edge 55 and at least a portion of the concave surface 59 or places the image of the leading edge 55 and at least a portion of the convex surface 61 of each of the rotor blades 52 of the gas turbine engine 10 onto corresponding positions of the model of the rotor 50 and rotor blades 52 and places the image of the trailing edge 57 and at least a portion of the convex surface 61 or places the image of the trailing edge 57 and at least a portion of the concave surface 59 of each of the rotor blades 52 of the gas turbine engine 10 onto corresponding positions of the model of the rotor 50 and rotor blades 52.

The image of each of the rotor blades 52 from each of the cameras 74 at the different longitudinal position of the boroscope 70 are supplied to the processor 78, the processor 78 producing a composite image of each of the rotor blades 52 from the images supplied by the plurality of cameras 74. The composite image of each of the rotor blades 52 of the gas turbine engine 10 are placed onto corresponding positions of the model of the rotor 50 and rotor blades 52.

The processor 78 also analyses the measurement of the angular position of the rotor 50 relative to the boroscopes 70 provided by the sensor 86 and the processor 78 relates the images of each of the rotor blades 52 to the corresponding rotor blade 52 on the rotor 50.

The method comprises inserting a boroscope 70 between two adjacent stator vanes 64 of the stage of stator vanes 64 upstream of the at least one stage of rotor blades 52 and inserting a boroscope 70 between two adjacent stator vanes 64 of the stage of stator vanes 64 downstream of the at least one stage of rotor blades 52. The method comprises placing a boroscope upstream 70 of each one of a plurality of stages of rotor blades 52 and placing a boroscope 70 downstream of each one of the plurality of stages of rotor blades 52 and comprises providing reference measurements of the rotor blades 52 of each of the stages of rotor blades 52 and/or reference measurements between the rotor blades 52 of each of the stages of rotor blades 52 and the corresponding boroscopes 70 and comprises analysing the images of the rotor blades 52 of each of the stages of rotor blades 52 and using the reference measurements of the rotor blades 52 for each stage of rotor blades 52 and/or reference measurements between the rotor blades 52 of each stage of rotor blades 52 and the corresponding boroscopes 70 to determine the position and size of any defect on any of the rotor blades 52.

Figure 5:
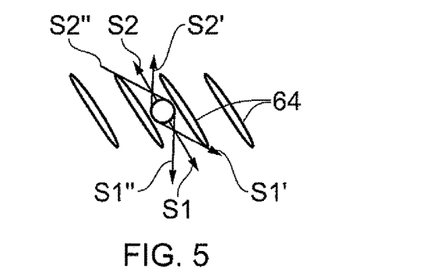
FIG. 5 is an alternative cross-sectional view in the direction of arrows A-A in FIG. 3.

FIG. 5 shows a boroscope 70 which comprises a plurality of cameras 74 at one or more of the predetermined longitudinal position and the cameras 74 are arranged with lines of sight S1, S1' and S1" directed in a downstream direction towards a stage 51B or 51C respectively of rotor blades 52 arranged at different angles and cameras 74 are arranged with lines of sight S2, S2' and S2" directed in an upstream direction towards a stage 51A or 51B respectively of rotor blades 52 arranged at different angles. This arrangement provides a greater amount of viewing capacity.

FIG. 6 shows a first type of boroscope 70A arranged to be inserted upstream of the first stage 51A of rotor blades 52. The boroscope 70A in this example has four cameras 74, each camera 74 is arranged at a respective one of four predetermined longitudinal positions on the boroscope 70A. Each of the cameras 74 is arranged with a line of sight directed towards the upstream edge 55 of the first stage, upstream stage, 51A of rotor blades 52.

FIG. 7 shows a second type of boroscope 70B arranged to be inserted downstream of the first stage 51A of rotor blades 52 and upstream of the second stage 51B of rotor blades 52. The boroscope 70B has seven cameras 74. Four of the cameras 74 are arranged with a line of sight directed towards the downstream edge 57 of the first stage, upstream stage, 51A of rotor blades 52. Three of the cameras 74 are arranged with a line of sight directed towards the upstream edge 55 of the second stage, upstream stage, 51B of rotor blades 52. Each camera 74 of the four cameras 74 with a line of sight directed towards the downstream edge 57 of the first stage, upstream stage, 51A of rotor blades 52 is arranged at a respective one of four predetermined longitudinal positions on the boroscope 70B. Each of the three cameras 74 with a line of sight directed towards the upstream edge 55 of the second stage 51B of rotor blades 52 is arranged at a respective one of three predetermined longitudinal positions on the boroscope 70B.

FIG. 8 shows another second type of boroscope 70C arranged to be inserted downstream of the one stage 51B of rotor blades 52 and upstream of another stage 51C of rotor blades 52. The boroscope 70C has six cameras 74. Three of the cameras 74 are arranged with a line of sight directed towards the downstream edge 57 of one stage 51B of rotor blades 52. Three of the cameras 74 are arranged with a line of sight directed towards the upstream edge 55 of the other stage 51C of rotor blades 52. Each camera 74 of the three cameras 74 with a line of sight directed towards the downstream edge 57 of one stage 51B of rotor blades 52 is arranged at a respective one of three predetermined longitudinal positions on the boroscope 70C. Each of the three cameras 74 with a line of sight directed towards the upstream edge 55 of the other stage 51C of rotor blades 52 is arranged at a respective one of three predetermined longitudinal positions on the boroscope 70C.

Figure 9:
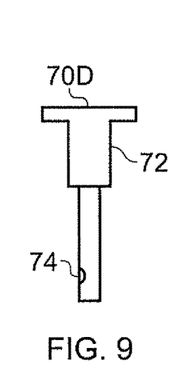
FIG. 9 is a view of a third type of boroscope of the apparatus for inspecting a gas turbine engine according to the present invention.

FIG. 9 shows a third type of boroscope 70D arranged to be inserted downstream of the last stage 51F of rotor blades 52. The boroscope has one camera 74 arranged at a predetermined longitudinal position on the boroscope 70D. The camera 74 is arranged with a line of sight directed towards the downstream edge 57 of the last stage, downstream stage, 51F of rotor blades 52.

The rotor 50 is only rotated through one full revolution so that each rotor blade 52 in each stage of rotor blades 52 is viewed and is imaged from both the leading edge 55 and the trailing edge 57 and a video is recorded. The present invention allows all the rotor blade stages 52 on the rotor 50 to be fully inspected within a few minutes of opening the cowling of the turbofan gas turbine engine 10.

In the present invention multiple data streams, e.g. from multiple USB cameras, are plugged into a management hub and inputted as a single data stream into the processor, personal computer. The videos may be displayed on a monitor and image analysis software is used to stitch the multiple data streams together to build a complete picture of the rotor, and rotor blades, and highlight any areas of interest, such as areas on any one or more of the rotor blades which has damage or erosion. The model in the processor may have the images of the rotor blades from the cameras painted, overlaid, on the surfaces of the corresponding rotor blades in the model in the processor. The use of multiple cameras each positioned at a fixed, known, point, together with the rotation of the rotor through a full revolution allows measurements to be taken from the images. Each of the apertures in the outer and inner casings is at a fixed, known, point and each of the boroscopes is located in a respective aperture in the outer casing and secured to the outer casing while in the respective aperture in the outer casing. Each of the cameras on each boroscope is at a fixed, known, point on the boroscope and thus the positions of the cameras within the gas turbine engine are known and the positions of the cameras relative to the rotor blades on the rotors are known.

Thus, the advantage of the present invention is that it allows an in-situ inspection of a gas turbine engine to be carried out within a few minutes compared to about 8 to 10 hours it currently takes to perform an in-situ inspection. Another advantage of the present invention is that the in-situ inspection process does not require highly skilled operators to perform the inspection process. A further advantage of the present invention is that the analysis of the images makes it easy for the operators to determine which component the images relate to. Furthermore, the data quality is better than the current in-situ inspection process.

The present invention has been described with reference to inspecting the rotor and rotor blades of the intermediate pressure compressor but the present invention is equally applicable to inspecting the rotor and rotor blades of the high pressure compressor, the rotor and rotor blades of the high pressure turbine, the rotor and rotor blades of the intermediate pressure turbine or the rotor and rotor blades of the low pressure turbine. The present invention may be also be used to inspect the rotor and rotor blades of the intermediate pressure compressor, the rotor and rotor blades of the high pressure compressor, the rotor and rotor blades of the high pressure turbine, the rotor and rotor blades of the intermediate pressure turbine and the rotor and rotor blades of the low pressure turbine all at the same time. The present invention may be also be used to inspect the rotor and rotor blades of the high pressure compressor, the rotor and rotor blades of the high pressure turbine and the rotor and rotor blades of the low pressure turbine all at the same time.

Although the present invention has been described with reference to inspecting a turbofan gas turbine engine, the present invention is equally applicable to inspecting a turbojet gas turbine engine, a turboshaft gas turbine engine or a turboprop gas turbine engine. The present invention is applicable to inspecting aero gas turbine engine, marine gas turbine engines or industrial gas turbine engines.

It is also possible to provide each boroscope with a data store and a data processor so that it is possible to do data processing at each boroscope and then subsequently download the data from each boroscope to the processor.

Although the present invention has been described with reference to inspecting gas turbine engines the present invention is equally applicable to inspecting other types of turbomachine, for example a steam turbine, a water turbine or a wind turbine.

The present invention also provides a method of inspecting a turbomachine, the turbomachine comprising a rotor having at least one stage of rotor blades and a casing surrounding the rotor and at least one stage of rotor blades, each rotor blade having a leading edge, a trailing edge, a concave surface and a convex surface, the method comprising the steps of a) providing a plurality of boroscopes, b) inserting each boroscope through a respective one of a plurality of apertures in a casing of the turbomachine, at least one of the apertures in the casing being upstream of the rotor blades, at least one of the apertures in the casing being downstream of the rotor blades, c) rotating the rotor of the turbomachine, d) providing a processor having a model of the rotor and the at least one stage of rotor blades, e) viewing the leading edge and at least a portion of the concave surface or viewing the leading edge and at least a portion of the convex surface of each of the rotor blades of the turbomachine as the rotor is rotated using the boroscope in the at least one of the apertures in the casing upstream of the rotor blades and supplying the image of each of the rotor blades to the processor, f) viewing the trailing edge and at least a portion of the convex surface or viewing the trailing edge and at least a portion of the concave surface of each of the rotor blades of the turbomachine as the rotor is rotated using the boroscope in the at least one of the apertures in the casing downstream of the rotor blades and supplying the image of each of the rotor blades to the processor, and g) placing the image of the leading edge and at least a portion of the concave surface or the leading edge and at least a portion of the convex surface of each of the rotor blades of the turbomachine onto corresponding positions of the model of the rotor and rotor blades and placing the image of the trailing edge and at least a portion of the convex surface or the trailing edge and at least a portion of the concave surface of each of the rotor blades of the turbomachine onto corresponding positions of the model of the rotor and rotor blades.

The invention claimed is:

1. A method of inspecting a turbomachine, the turbomachine comprising a rotor having at least one stage of rotor blades and a casing surrounding the rotor and at least one stage of rotor blades, each rotor blade comprising a platform portion and an aerofoil portion, the aerofoil portion having a leading edge, a trailing edge, a concave surface, a convex surface and a tip, the method comprising the steps of:
   a) providing a plurality of boroscopes,
   b) inserting each boroscope through a respective one of a plurality of apertures in a casing of the turbomachine, at least one of the apertures in the casing being upstream of the rotor blades, at least one of the apertures in the casing being downstream of the rotor blades,
   c) rotating the rotor of the turbomachine,
   d) viewing the leading edge and at least a portion of the concave surface or viewing the leading edge and at least a portion of the convex surface of each of the rotor blades of the turbomachine as the rotor is rotated using the boroscope in the at least one of the apertures in the casing upstream of the rotor blades and supplying the image of each of the rotor blades to a processor,
   e) viewing the trailing edge and at least a portion of the convex surface or viewing the trailing edge and at least a portion of the concave surface of each of the rotor blades of the turbomachine as the rotor is rotated using the boroscope in the at least one of the apertures in the casing downstream of the rotor blades and supplying the image of each of the rotor blades to the processor, and
   f) displaying the images of the rotor blades.

2. The method according to claim 1, comprising providing a model of the rotor and the at least one stage of rotor blades.

3. The method according to claim 2, comprising:
   placing the image of the leading edge and at least a portion of the concave surface or placing the image of the leading edge and at least a portion of the convex surface of each of the rotor blades of the turbomachine onto corresponding positions of the model of the rotor and rotor blades, and
   placing the image of the trailing edge and at least a portion of the convex surface or placing the image of the trailing edge and at least a portion of the concave surface of each of the rotor blades of the turbomachine onto corresponding positions of the model of the rotor and rotor blades.

4. The method according to claim 1, wherein each boroscope comprises a rigid structure and at least one camera arranged at a predetermined longitudinal position, the at least one camera is arranged with a line of sight transverse to the longitudinal direction of the boroscope.

5. The method according to claim 4, wherein at least one of the boroscopes comprises a plurality of cameras.

6. The method according to claim 5, wherein at least one of the boroscopes comprises a plurality of cameras at the predetermined longitudinal position and the cameras are arranged with lines of sight arranged at different angles.

7. The method according to claim 5, wherein at least one of the boroscopes comprises a plurality of cameras at different longitudinal positions.

8. The method according to claim 7, further comprising supplying the image of each of the rotor blades from each of the cameras at the different longitudinal positions of the boroscope to the processor, the processor producing a composite image of each of the rotor blades from the images supplied by the plurality of cameras.

9. The method according to claim 8, further comprising placing the composite image of each of the rotor blades of the turbomachine onto corresponding positions of the model of the rotor and rotor blades.

10. The method according to claim 5, wherein at least one of the boroscopes comprises at least one camera arranged with a line of sight directed in a downstream direction towards a stage of rotor blades and at least one camera arranged with a line of sight directed in an upstream direction towards a stage of rotor blades.

11. The method according to claim 1, wherein:
the turbomachine comprises a stage of stator vanes upstream of the at least one stage of rotor blades and a stage of stator vanes downstream of the at least one stage of rotor blades, and
step b) comprises inserting a boroscope between two adjacent stator vanes of the stage of stator vanes upstream of the at least one stage of rotor blade and inserting a boroscope between two adjacent stator vanes of the stage of stator vanes downstream of the at least one stage of rotor blades.

12. The method according to claim 1, wherein:
step (b) comprises placing a boroscope upstream of each one of a plurality of stages of rotor blades and placing a boroscope downstream of each one of the plurality of stages of rotor blades,
step d) comprises providing reference measurements of the rotor blades of each of the stages of rotor blades and/or reference measurements between the rotor blades of each of the stages of rotor blades and the corresponding boroscopes, and
step f) comprises analysing the images of the rotor blades of each of the stages of rotor blades and using the reference measurements of the rotor blades for each stage of rotor blades and/or reference measurements between the rotor blades of each stage of rotor blades and the corresponding boroscopes to determine the position and size of any defect on any of the rotor blades.

13. The method according to claim 1, wherein the rotor is a compressor rotor and the rotor blades are compressor blades.

14. The method according to claim 1, wherein the rotor is a turbine rotor and the rotor blades are turbine blades.

15. The method according to claim 1, further comprising performing data processing for at least one of the boroscopes and supplying processed data to the processor.

16. The method according to claim 1, further comprising measuring the angular position of the rotor relative to the boroscope and relating the image of each rotor blade to the corresponding rotor blade on the rotor.

17. An apparatus for inspecting a turbomachine,
the turbomachine comprising a rotor having at least one stage of rotor blades and a casing surrounding the rotor and at least one stage of rotor blades,
each rotor blade comprising a platform portion and an aerofoil portion,
the aerofoil portion having a leading edge, a trailing edge, a concave surface, a convex surface and a tip,
the casing of the turbomachine having a plurality of apertures, at least one of the apertures in the casing being upstream of the rotor blades and at least one of the apertures in the casing being downstream of the rotor blades,
the apparatus comprising:
a plurality of boroscopes, each boroscope being insertable through a respective one of the plurality of apertures in the casing of the turbomachine;
a device to rotate the rotor of the turbomachine; and
a processor,
at least one of the boroscopes inserted in at least one of the apertures in the casing upstream of the rotor blades being arranged to view the leading edge and at least a portion of the concave surface or being arranged to view the leading edge and at least a portion of the convex surface of each of the rotor blades of the turbomachine as the rotor is rotated,
the at least one of the boroscopes being arranged to supply the image of the leading edge and at least a portion of the concave surface or being arranged to supply the image of the leading edge and at least a portion of the convex surface of each of the rotor blades of the turbomachine to the processor as the rotor is rotated,
at least one of the boroscopes inserted in at least one of the apertures in the casing downstream of the rotor blades being arranged to view trailing edge and at least a portion of the convex surface or being arranged to view the trailing edge and at least a portion of the concave surface of each of the rotor blades of the turbomachine as the rotor is rotated,
the at least one of the boroscopes being arranged to supply the image of the trailing edge and at least a portion of the convex surface or being arranged to supply the image of the trailing edge and at least a portion of the concave surface of each of the rotor blades of the turbomachine to the processor as the rotor is rotated,
the processor being arranged to display the images of the rotor blades.

18. A method of inspecting a turbomachine, the turbomachine comprising a rotor having a plurality of stages of rotor blades and a casing surrounding the rotor and the plurality of stages of rotor blades, each rotor blade comprising a platform portion and an aerofoil portion, the aerofoil portion having a leading edge, a trailing edge, a concave surface, a convex surface and a tip,
the method comprising the steps of:
a) providing a plurality of boroscopes,
b) inserting each boroscope through a respective one of a plurality of apertures in a casing of the turbomachine, each aperture in the casing being upstream of a respective stage of rotor blades, at least one of the apertures in the casing being downstream of a stage rotor blades,
c) rotating the rotor of the turbomachine, d) viewing the leading edge and at least a portion of the concave surface or viewing the leading edge and at least a portion of the convex surface of each of the rotor blades of each of the stages of rotor blades of the turbomachine as the rotor is rotated using the boroscopes in the apertures in the casing upstream of each of the stages of rotor blades and supplying the image of each of the rotor blades of each of the stages of rotor blades to a processor, and e) displaying the images of the rotor blades.

19. A method of inspecting a turbomachine, the turbomachine comprising a rotor having a plurality of stages of rotor blades and a casing surrounding the rotor and the plurality of stages of rotor blades, each rotor blade comprising a platform portion and an aerofoil portion, the aerofoil portion having a leading edge, a trailing edge, a concave surface, a convex surface and a tip, the method comprising the steps of:
 a) providing a plurality of boroscopes,
 b) inserting each boroscope through a respective one of a plurality of apertures in a casing of the turbomachine, each aperture in the casing being downstream of a respective stage of rotor blades, at least one of the apertures in the casing being upstream of a stage rotor blades,
 c) rotating the rotor of the turbomachine,
 d) viewing the trailing edge and at least a portion of the concave surface or viewing the trailing edge and at least a portion of the convex surface of each of the rotor blades of each of the stages of rotor blades of the turbomachine as the rotor is rotated using the boroscopes in the apertures in the casing downstream of each of the stages of rotor blades and supplying the image of each of the rotor blades of each of the stages of rotor blades to a processor, and
 e) displaying the images of the rotor blades.

20. A method of inspecting a turbomachine, the turbomachine comprising a rotor having at least one stage of rotor blades and a casing surrounding the rotor and at least one stage of rotor blades, each rotor blade comprising a platform portion and an aerofoil portion, the aerofoil portion having a leading edge, a trailing edge, a concave surface, a convex surface and a tip, the method comprising the steps of:
 a) providing a plurality of boroscopes,
 b) inserting each boroscope through a respective one of a plurality of apertures in a casing of the turbomachine, at least one of the apertures in the casing being upstream of the rotor blades, at least one of the apertures in the casing being downstream of the rotor blades,
 c) rotating the rotor of the turbomachine,
 d) providing a processor having a model of the rotor and the at least one stage of rotor blades,
 e) viewing the leading edge and at least a portion of the concave surface or viewing the leading edge and at least a portion of the convex surface of each of the rotor blades of the turbomachine as the rotor is rotated using the boroscope in the at least one of the apertures in the casing upstream of the rotor blades and supplying the image of each of the rotor blades to the processor,
 f) viewing the trailing edge and at least a portion of the convex surface or viewing the trailing edge and at least a portion of the concave surface of each of the rotor blades of the turbomachine as the rotor is rotated using the boroscope in the at least one of the apertures in the casing downstream of the rotor blades and supplying the image of each of the rotor blades to the processor, and
 g) placing the image of the leading edge and at least a portion of the concave surface or the leading edge and at least a portion of the convex surface of each of the rotor blades of the turbomachine onto corresponding positions of the model of the rotor and rotor blades and placing the image of the trailing edge and at least a portion of the convex surface or the trailing edge and at least a portion of the concave surface of each of the rotor blades of the turbomachine onto corresponding positions of the model of the rotor and rotor blades.

* * * * *